United States Patent
Lee et al.

(10) Patent No.: US 9,321,821 B2
(45) Date of Patent: Apr. 26, 2016

(54) COSMETIC COMPOSITION FOR IMPROVING SKIN CONDITIONS COMPRISING FUSION PROTEIN

(71) Applicant: LG Household & Health Care Ltd., Seoul (KR)

(72) Inventors: Seol Hoon Lee, Daejeon (KR); Sang Hwa Lee, Daejeon (KR); Nae Gyu Kang, Daejeon (KR); Eu Gene Hur, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 14/265,537

(22) Filed: Apr. 30, 2014

(65) Prior Publication Data

US 2015/0133379 A1     May 14, 2015

(30) Foreign Application Priority Data

| Nov. 14, 2013 | (KR) | 10-2013-0138657 |
| Nov. 14, 2013 | (KR) | 10-2013-0138658 |
| Feb. 21, 2014 | (KR) | 10-2014-0020768 |
| Feb. 21, 2014 | (KR) | 10-2014-0020769 |
| Feb. 21, 2014 | (KR) | 10-2014-0020770 |
| Feb. 21, 2014 | (KR) | 10-2014-0020771 |

(51) Int. Cl.

| A61K 38/18 | (2006.01) |
| C07K 14/61 | (2006.01) |
| C07K 14/485 | (2006.01) |
| C07K 14/49 | (2006.01) |
| C07K 14/50 | (2006.01) |
| A61K 8/64 | (2006.01) |
| A61Q 19/08 | (2006.01) |
| A61Q 19/00 | (2006.01) |
| A61Q 19/02 | (2006.01) |
| A61K 38/00 | (2006.01) |

(52) U.S. Cl.
CPC . *C07K 14/50* (2013.01); *A61K 8/64* (2013.01); *A61Q 19/007* (2013.01); *A61Q 19/02* (2013.01); *A61Q 19/08* (2013.01); *C07K 14/485* (2013.01); *C07K 14/49* (2013.01); *A61K 38/00* (2013.01)

(58) Field of Classification Search
None
See application file for complete search history.

(56) References Cited

U.S. PATENT DOCUMENTS

| 7,659,252 B2 | 2/2010 | Wen et al. |
| 8,518,871 B2 | 8/2013 | Hsu et al. |

FOREIGN PATENT DOCUMENTS

| JP | 08-208424 | 8/1996 |
| JP | 08-231370 | 9/1996 |
| JP | 10-036283 | 2/1998 |
| KR | 10-2011-0004718 A | 1/2011 |
| KR | 10-2011-0049346 A | 6/2011 |
| KR | 101329411 B1 | 11/2013 |

OTHER PUBLICATIONS

Ruan et al., "Transdermal delivery of human epidermal growth factor facilitated by a peptide chaperon," European J. of Medicinal Chem., vol. 62, pp. 405-409, Jan. 11, 2013.
First Office Action, Chinese Patent Application No. 10-2014-0020768, China State Intellectual Property Office, Jul. 14, 2015.
First Office Action, Chinese Patent Application No. 10-2014-0020769, China State Intellectual Property Office, Jul. 10, 2015.
First Office Action, Chinese Patent Application No. 10-2014-0020770, China State Intellectual Property Office, Jul. 14, 2015.
Lee et al., "Selection of Skin-Penetrating Peptide Using Phage Display," Yakhak Hoeji, vol. 57, No. 2, pp. 125-131, Apr. 30, 2013.

*Primary Examiner* — Christine J Saoud
(74) *Attorney, Agent, or Firm* — Joseph R. Baker, Jr.; Gavrilovich, Dodd & Lindsey LLP

(57) ABSTRACT

The present invention relates to a fusion protein comprising a skin-penetrating peptide, a polynucleotide encoding the fusion protein, an expression vector comprising the polynucleotide, a transformant comprising the expression vector, a method for preparing the fusion protein, a cosmetic composition for improving skin conditions, which comprises the fusion protein, and a pharmaceutical composition for external skin use, which comprises the fusion protein. The fusion protein of the invention comprises a skin-penetrating peptide bound to a physiologically active protein. The fusion protein significantly enhances the skin penetration and skin retention of the physiologically active protein while maintaining or enhancing the ability of the physiologically active protein to synthesize a material showing physiologically active effects. Thus, it can be widely used as an active ingredient in functional cosmetic compositions and pharmaceutical compositions for external skin use.

6 Claims, No Drawings

SEQUENCE LISTING

```
<160> NUMBER OF SEQ ID NOS: 10

<210> SEQ ID NO 1
<211> LENGTH: 12
<212> TYPE: PRT
<213> ORGANISM: Artificial Sequence
<220> FEATURE:
<223> OTHER INFORMATION: Transdermal Peptide

<400> SEQUENCE: 1

Asn Gly Ser Leu Asn Thr His Leu Ala Pro Ile Leu
1               5                   10

<210> SEQ ID NO 2
<211> LENGTH: 142
<212> TYPE: PRT
<213> ORGANISM: Artificial Sequence
<220> FEATURE:
<223> OTHER INFORMATION: hGH fragment

<400> SEQUENCE: 2

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr
    130                 135                 140

<210> SEQ ID NO 3
<211> LENGTH: 53
<212> TYPE: PRT
<213> ORGANISM: Artificial Sequence
<220> FEATURE:
<223> OTHER INFORMATION: EGF

<400> SEQUENCE: 3

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30
```

```
Cys Val Val Gly Tyr Ile Glu Arg Cys Gln Tyr Arg Asp Leu Lys
        35                  40                  45

Trp Trp Glu Leu Arg
 50
```

<210> SEQ ID NO 4
<211> LENGTH: 109
<212> TYPE: PRT
<213> ORGANISM: Artificial Sequence
<220> FEATURE:
<223> OTHER INFORMATION: PDGFb fragment

<400> SEQUENCE: 4

```
Ser Leu Gly Ser Leu Thr Ile Ala Glu Pro Ala Met Ile Ala Glu Cys
 1               5                   10                  15

Lys Thr Arg Thr Glu Val Phe Glu Ile Ser Arg Arg Leu Ile Asp Arg
                20                  25                  30

Thr Asn Ala Asn Phe Leu Val Trp Pro Pro Cys Val Glu Val Gln Arg
            35                  40                  45

Cys Ser Gly Cys Cys Asn Asn Arg Asn Val Gln Cys Arg Pro Thr Gln
 50                  55                  60

Val Gln Leu Arg Pro Val Gln Val Arg Lys Ile Glu Ile Val Arg Lys
 65                  70                  75                  80

Lys Pro Ile Phe Lys Lys Ala Thr Val Thr Leu Glu Asp His Leu Ala
                85                  90                  95

Cys Lys Cys Glu Thr Val Ala Ala Ala Arg Pro Val Thr
                100                 105
```

<210> SEQ ID NO 5
<211> LENGTH: 155
<212> TYPE: PRT
<213> ORGANISM: Artificial Sequence
<220> FEATURE:
<223> OTHER INFORMATION: bFGF

<400> SEQUENCE: 5

```
Met Ala Ala Gly Ser Ile Thr Thr Leu Pro Ala Leu Pro Glu Asp Gly
 1               5                   10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155
```

<210> SEQ ID NO 6

```
<211> LENGTH: 156
<212> TYPE: PRT
<213> ORGANISM: Artificial Sequence
<220> FEATURE:
<223> OTHER INFORMATION: hGH fusion protein

<400> SEQUENCE: 6

Asn Gly Ser Leu Asn Thr His Leu Ala Pro Ile Leu Gly Gly Phe Pro
1               5                   10                  15

Thr Ile Pro Leu Ser Arg Leu Phe Asp Asn Ala Met Leu Arg Ala His
            20                  25                  30

Arg Leu His Gln Leu Ala Phe Asp Thr Tyr Gln Glu Phe Glu Glu Ala
        35                  40                  45

Tyr Ile Pro Lys Glu Gln Lys Tyr Ser Phe Leu Gln Asn Pro Gln Thr
    50                  55                  60

Ser Leu Cys Phe Ser Glu Ser Ile Pro Thr Pro Ser Asn Arg Glu Glu
65                  70                  75                  80

Thr Gln Gln Lys Ser Asn Leu Glu Leu Leu Arg Ile Ser Leu Leu Leu
                85                  90                  95

Ile Gln Ser Trp Leu Glu Pro Val Gln Phe Leu Arg Ser Val Phe Ala
            100                 105                 110

Asn Ser Leu Val Tyr Gly Ala Ser Asp Ser Asn Val Tyr Asp Leu Leu
        115                 120                 125

Lys Asp Leu Glu Glu Gly Ile Gln Thr Leu Met Gly Arg Leu Glu Asp
    130                 135                 140

Gly Ser Pro Arg Thr Gly Gln Ile Phe Lys Gln Thr
145                 150                 155

<210> SEQ ID NO 7
<211> LENGTH: 67
<212> TYPE: PRT
<213> ORGANISM: Artificial Sequence
<220> FEATURE:
<223> OTHER INFORMATION: fusion protein (T-EGF)

<400> SEQUENCE: 7

Asn Gly Ser Leu Asn Thr His Leu Ala Pro Ile Leu Gly Gly Asn Ser
1               5                   10                  15

Asp Ser Glu Cys Pro Leu Ser His Asp Gly Tyr Cys Leu His Asp Gly
            20                  25                  30

Val Cys Met Tyr Ile Glu Ala Leu Asp Lys Tyr Ala Cys Asn Cys Val
        35                  40                  45

Val Gly Tyr Ile Gly Glu Arg Cys Gln Tyr Arg Asp Leu Lys Trp Trp
    50                  55                  60

Glu Leu Arg
65

<210> SEQ ID NO 8
<211> LENGTH: 123
<212> TYPE: PRT
<213> ORGANISM: Artificial Sequence
<220> FEATURE:
<223> OTHER INFORMATION: fusion protein (T-PDGFb)

<400> SEQUENCE: 8

Asn Gly Ser Leu Asn Thr His Leu Ala Pro Ile Leu Gly Gly Ser Leu
1               5                   10                  15

Gly Ser Leu Thr Ile Ala Glu Pro Ala Met Ile Ala Glu Cys Lys Thr
            20                  25                  30
```

```
Arg Thr Glu Val Phe Glu Ile Ser Arg Arg Leu Ile Asp Arg Thr Asn
            35                  40                  45
Ala Asn Phe Leu Val Trp Pro Pro Cys Val Glu Val Gln Arg Cys Ser
 50                      55                  60
Gly Cys Cys Asn Asn Arg Asn Val Gln Cys Arg Pro Thr Gln Val Gln
 65                  70                  75                  80
Leu Arg Pro Val Gln Val Arg Lys Ile Glu Ile Val Arg Lys Lys Pro
                85                  90                  95
Ile Phe Lys Lys Ala Thr Val Thr Leu Glu Asp His Leu Ala Cys Lys
                100                 105                 110
Cys Glu Thr Val Ala Ala Ala Arg Pro Val Thr
                115                 120
```

<210> SEQ ID NO 9
<211> LENGTH: 169
<212> TYPE: PRT
<213> ORGANISM: Artificial Sequence
<220> FEATURE:
<223> OTHER INFORMATION: fusion protein (T-bFGF)

<400> SEQUENCE: 9

```
Asn Gly Ser Leu Asn Thr His Leu Ala Pro Ile Leu Gly Gly Met Ala
 1               5                  10                  15
Ala Gly Ser Ile Thr Thr Leu Pro Ala Leu Pro Glu Asp Gly Gly Ser
                20                  25                  30
Gly Ala Phe Pro Pro Gly His Phe Lys Asp Pro Lys Arg Leu Tyr Cys
                35                  40                  45
Lys Asn Gly Gly Phe Phe Leu Arg Ile His Pro Asp Gly Arg Val Asp
 50                  55                  60
Gly Val Arg Glu Lys Ser Asp Pro His Ile Lys Leu Gln Leu Gln Ala
 65                  70                  75                  80
Glu Glu Arg Gly Val Val Ser Ile Lys Gly Val Cys Ala Asn Arg Tyr
                85                  90                  95
Leu Ala Met Lys Glu Asp Gly Arg Leu Leu Ala Ser Lys Cys Val Thr
                100                 105                 110
Asp Glu Cys Phe Phe Phe Glu Arg Leu Glu Ser Asn Asn Tyr Asn Thr
                115                 120                 125
Tyr Arg Ser Arg Lys Tyr Thr Ser Trp Tyr Val Ala Leu Lys Arg Thr
                130                 135                 140
Gly Gln Tyr Lys Leu Gly Ser Lys Thr Gly Pro Gly Gln Lys Ala Ile
145                 150                 155                 160
Leu Phe Leu Pro Met Ser Ala Lys Ser
                165
```

<210> SEQ ID NO 10
<211> LENGTH: 5
<212> TYPE: PRT
<213> ORGANISM: Artificial Sequence
<220> FEATURE:
<223> OTHER INFORMATION: Artificial cleavable peptide sequence

<400> SEQUENCE: 10

```
Asp Asp Asp Asp Lys
 1               5
```

COSMETIC COMPOSITION FOR IMPROVING SKIN CONDITIONS COMPRISING FUSION PROTEIN

CROSS REFERENCE TO RELATED APPLICATIONS

This application claims priority to Korean Patent Application No. 10-2013-0138657, filed 14 Nov. 2013 (14 Nov. 2013); Korean Patent Application No. 10-2013-0138658, filed 14 Nov. 2013 (14 Nov. 2013); Korean Patent Application No. 10-2014-0020768, filed 21 Feb. 2014 (21 Dec. 2014); Korean Patent Application No. 10-2014-0020769, filed 21 Feb. 2014 (21 Feb. 2014); Korean Patent Application No. 10-2014-0020770, filed 21 Feb. 2014 (21 Feb. 2014); and Korean Patent Application No. 10-2014-0020771, filed 21 Feb. 2014 (21 Feb. 2014), the disclosure of which are incorporated herein by reference in their entirety.

FIELD OF THE INVENTION

The present invention relates to a fusion protein comprising a skin-penetrating peptide, a polynucleotide encoding the fusion protein, an expression vector comprising the polynucleotide, a transformant comprising the expression vector, a method for preparing the fusion protein, a cosmetic composition for improving skin conditions which comprises the fusion protein, and a pharmaceutical composition for external skin use which comprises the fusion protein.

BACKGROUND

With continued developments in the cosmetic industry, highly functional cosmetics have been continuously developed using new materials and technologies. In addition, in recent years, the amount of consumers who demand specific effects including skin whitening, wrinkle reduction and skin regeneration has increased, and as such the value of functional cosmetics in the cosmetic industry has further increased, and studies on the application of various materials to cosmetics have received attention.

For example, skin wrinkles can be said to be morphological and structural changes in the skin, which occur locally in regions that undergo permanent deformation due to muscular motion. In order to understand the wrinkle formation mechanism, it is important to investigate not only such physiological changes, but also changes in the internal structure and physical properties of the skin. In connection with this, reported changes in the internal structure of the skin, which are caused by photoaging, include thickening of the epidermis and dermis, abnormal accumulation of elastotic material, and changes in the three-dimensional structure of elastic fiber. In addition, with respect to collagen, which is the major component of skin, microfibrillation of collagen fibers, weakening of fibers, and the like have been reported.

Collagen is a major matrix protein that is produced in skin fibroblasts. It is an important protein that is present in the extracellular matrix and accounts for 30 wt % of the total weight of the proteins in the body. It also has a rigid triple-helical structure. It is known that collagen mainly functions to give mechanical firmness to the skin, strengthen connective tissue, bind tissues, maintain cell adhesion, and induce cell division and differentiation (during organism growth or wound healing). The amount of collagen proteins decreases with age and with UV-induced photoaging. As is generally known in the art, as aging progresses, the skin becomes thinner, and this phenomenon is closely associated with a decrease in skin elasticity and the formation of wrinkles.

Active ingredients known to exhibit wrinkle reduction effects by promoting collagen synthesis include, for example, retinoic acid, TGF (transforming growth factor), animal placenta-derived protein (Japanese Patent Laid-Open Publication No. 1996-231370), betulinic acid (Japanese Patent Laid-Open Publication No. 1996-208424), chlorella extracts (Japanese Patent Laid-Open Publication Nos. 1994-040523 and 1998-036283) and the like. However, these active ingredients have a problem in that they may cause side effects, such as irritation and redness, upon application to the skin and thus have had limited applications. Alternatively, these active ingredients have insignificant effects, and thus cannot provide a sufficient effect of improving skin conditions by promoting collagen synthesis in the skin.

It is known that this problem is mainly because the various active ingredients intended to exhibit wrinkle reduction effects by promoting collagen synthesis are not normally absorbed into the skin. Thus, studies have been actively conducted to develop methods for promoting the absorption of the above-described active ingredients. For example, Korean Patent Registration No. 1054519 discloses a human growth hormone-derived peptide having excellent stability and skin penetration properties compared to natural human growth hormones, and a composition comprising the same, and Korean Patent Registration No. 1104223 discloses an IL-10-derived peptide, which performs the same function as that of human IL-10 and has very excellent stability and skin penetration properties compared to natural IL-10, and a composition comprising the same. However, these peptides have a disadvantage in that they merely exhibit functionality by themselves and cannot be used as carriers for delivering other drugs. This disadvantage suggests that excellent skin penetration alone does not satisfy the requirements for drug delivery. Thus, in order to promote collagen synthesis, it is required to develop novel materials that satisfy two requirements: excellent skin penetration, and enhancement of collagen synthesis in the skin. However, the results of dedicated studies on such materials have not yet been reported.

SUMMARY OF THE INVENTION

Accordingly, the present inventors have made extensive efforts to develop novel materials satisfying two requirements: excellent skin penetration, and the maintenance or enhancement of synthesis of physiologically active materials in the skin. As a result, the present inventors have developed a skin-penetrating peptide, which can be used as a carrier for transdermal delivery of drugs and, at the same time, can remain in the skin, and have found that a fusion protein comprising the skin-penetrating peptide and a physiologically active protein has excellent skin penetration ability while maintaining or enhancing the synthesis of physiologically active materials, such as collagen, elastin, laminin and HAS2, in the skin, thereby completing the present invention.

It is an object of the present invention to provide a fusion protein comprising a skin-penetrating peptide.

Another object of the present invention is to provide a polynucleotide encoding the fusion protein, an expression vector comprising the polynucleotide, and a transformant comprising the expression vector.

Still another object of the present invention is to provide a method for preparing a fusion protein comprising a skin-penetrating peptide, the method comprising the steps of: (a) culturing the transformant to obtain a culture product; and (b) recovering the fusion protein from the culture product.

Still another object of the present invention is to provide a cosmetic composition for improving skin conditions, which comprises the fusion protein as an active ingredient, and a method for improving skin conditions, which comprises transdermally administering the composition.

Still another object of the present invention is to provide a pharmaceutical composition for external skin use, which comprises the fusion protein.

DETAILED DESCRIPTION

The present inventors have conducted various studies to develop a novel material that has excellent skin penetration and skin retention properties while maintaining or enhancing the synthesis of physiologically active substances. During such studies, the present inventors have conducted a phage display consisting of a combination of elution test methods using a phage library and a transdermal agent, and as a result, have discovered a novel skin-penetrating peptide represented by the amino acid of SEQ ID NO: 1. In addition, the present inventors have fused the discovered skin-penetrating peptide with various physiologically active materials such as growth factors and hormones and screened fusion proteins showing excellent skin penetration ability and high levels of synthesis of physiologically active materials, and as a result, have found that a fusion protein comprising a physiologically active protein, such as a hormone or a cytokine, fused to the skin-penetrating peptide, has excellent skin penetration and retention properties while maintaining or enhancing the expression levels of physiologically active materials by the physiologically active protein.

Therefore, the fusion protein can be used as an active ingredient in functional cosmetic compositions and pharmaceutical compositions for external skin use.

In one aspect, the present invention provides a fusion protein comprising a skin-penetrating peptide represented by the amino acid sequence of SEQ ID NO: 1.

As used herein, the term "skin-penetrating" or "skin penetration" refers to the ability of the peptide to penetrate the skin, and the term "skin-penetrating peptide" refers to a peptide that has a skin penetration ability or the effect of enhancing the same.

As used herein, the term "skin retention" refers to the ability of a peptide that penetrated the skin to bind to skin tissue to remain in the skin without being delivered to the circulatory system through skin tissue. Pharmaceutical formulations or cosmetic formulations that target skin tissue preferably use a carrier that has an excellent property of remaining in skin tissue so that the component bound to the peptide can act on skin tissue or skin cells. The peptide of the present invention is excellent not only in terms of skin penetration, but also in terms of skin retention, and thus can be used as a carrier for a pharmaceutical or cosmetic formulation that targets skin tissue.

In the present invention, the skin-penetrating peptide may be a peptide having excellent skin penetration and skin retention properties, discovered by performing a phage display method consisting of a combination of elution test methods using a phage library and a transdermal agent. Preferably, it may be a peptide represented by amino acid sequence of SEQ ID NO: 1.

Preferably, the fusion protein may comprise the skin-penetrating peptide and a physiologically active protein.

As used herein, the term "physiologically active protein" refers to all proteins that are used for therapeutic effects.

The term "physiologically active protein" in the present invention collectively refers to proteins that regulate biological functions (physiological functions). The term is interchangeable with the term "physiologically active peptide". The physiologically active protein that is used in the present invention may be any protein that may be used to treat the skin. In addition, any derivative of the physiologically active protein also falls within the scope of the physiologically active peptide of the present invention, as long as it has substantially the same or enhanced function, structure, activity or stability compared to a wild-type protein.

More preferably, the physiologically active protein may be a hormone or a cytokine.

As used herein, the term "hormone" collectively refers to physiologically active proteins that are produced in, for example, the endocrine organ of the body. The hormone can be delivered to various organs in vivo through blood vessels to perform its function. Generally, the hormone can be involved in metabolism, reproduction, cell proliferation and the like, and can be synthesized in vivo or can be chemically synthesized.

In an embodiment of the present invention, the hormone may be a human growth hormone.

As used herein, the term "human growth hormone (hGH)" refers to a protein hormone that is secreted from the anterior pituitary. The human growth hormone functions to stimulate the differentiation of growth plate chondrocytes to promote growth. If the in vivo synthesis and secretion of the growth hormone is deficient, short stature, an increase in the risk of cardiovascular diseases, a decrease in muscle and bone density, etc., may occur. Preferably, the human growth hormone (hGH) may be a peptide represented by the amino acid sequence of SEQ ID NO: 2.

As used herein, the term "cytokine" collectively refers to physiologically active proteins that are secreted from cells. The cytokine selected from cells functions to regulate the physiological activity of other cells.

Preferably, the cytokine may be a growth factor.

As used herein, the term "growth factor" collectively refers to materials required for the proliferation of cells and the proliferation and growth of organisms, including polypeptides functioning to promote the division, growth and differentiation of cells. The kinds and functions of growth factors are diverse, and growth factors are also known to be involved in cell signaling. Thus, the supply of this growth factor to the skin can assist in the regeneration of the skin and promote the growth of skin cells. However, there have been problems in that this growth factor is difficult to penetrate into skin due to the defense mechanisms of skin and due to the fact that it binds to receptors on the skin surface so that it is rapidly internalized and degraded, and thus cannot remain on the skin surface for a long period of time.

In an embodiment of the present invention, the growth factor may be epithelial growth factor, platelet-derived growth factor-b subunit, or basic fibroblast growth factor.

As used herein, the term "epidermal growth factor (EGF)" is a polypeptide, also called as urogastrone, which comprises 53 amino acids and 3 disulfide bonds and has a molecular weight of 6045 Da. It is known that the epidermal growth factor mainly functions to stimulate the regeneration and differentiation of intestinal mucosa, corneal tissue and lung tissue, thereby promoting epidermal proliferation, blood vessel formation and wound healing and inhibiting gastric acid secretion (Senderoff, et al., Aqueous stability of human epidermal growth factor, Pharm. Res., 11, 1-48 (1994), Carpenter et al., Epidermal growth factor (EGF). Annu. Rev. Biochem. 48, 193-216 (1979)). Due to such functions, EGF has been developed and widely used as a wound healing treatment, and in recent years, EGF has been demonstrated to have wrinkle reduction or anti-aging effects, and thus has received attention as a functional cosmetic base material (Brown, G. L, U.S. Pat. No. 5,618,544).

As used herein, the term "platelet-derived growth factor subunit-b (PDGFb)" refers to a protein which belongs to the platelet-derived growth factor (PDGF) family, is contained in blood platelets and has a size of about 14 kDa. PDGF present in platelets is divided into subunit A having a size of about 18 kDa and subunit B as described. It is known that these subunits form the homodimer PDGF-AA or PDGF-BB or the heterodimer PDGF-AB by a disulfide bond.

As used herein, the term "basic fibroblast growth factor (bFGF)" is also called "FGF2" or "FGF-β, which is a double helical peptide having a size of about 18 kDa and an isoelectric point of 9.0 and showing the capability to bind to heparin. It is known that bFGF is mostly produced in the vascular epithelial cells and epidermal cells of organs, is stored in a state bound to the extracellular matrix, and binds to basic fibroblast growth factor receptors in cells to exhibit various functions, including angiogenesis, cell proliferation promotion, and differentiation induction.

In the present invention, the amino acid sequences of growth factors such as hGH, EGF, PDGFb and bFGF are not specifically limited, as long as they show the effect of maintaining or enhancing the synthesis of collagen, elastin, laminin and/or HAS2. In the present invention, the full-length amino acid sequence of the growth factor, a mutated amino acid sequence thereof, or a fragment thereof may be used. Information on the specific amino acid sequences of the growth factors and the nucleotide sequences of genes encoding the same are available from known databases such as the NCBI GenBank (GenBank Accession No. AAA35891.1, AAS83395.1, AAH92277.1, NP_002599, NP_035187, NP_001997, NP_032032, etc.).

Preferably, the EGF may be a peptide represented by the amino acid sequence of SEQ ID NO: 3, the PDGFb may be a peptide represented by the amino acid sequence of SEQ ID NO: 4, and the bFGF may be a peptide represented by the amino acid sequence of SEQ ID NO: 5.

As used herein, the term "fusion protein" refers to a peptide artificially synthesized so that the skin-penetrating peptide is bound to another protein or peptide. Preferably, the fusion peptide may be synthesized so that the skin-penetrating peptide is bound to a physiologically active peptide.

In the fusion protein according to the present invention, the skin-penetrating peptide may be linked directly or via a linker to the N-terminus of the physiologically active protein. The linker is not specifically limited, as long as it shows the effect of enhancing the activity of the esterase fusion protein. Preferably, the linker that is used in the present invention may be one or more selected from among amino acids such as glycine, alanine, leucine, iso-leucine, proline, serine, threonine, aspargine, aspartic acid, cysteine, glutamine, glutamic acid, lysine, and argininic acid. More preferably, the linker may be one or more amino acids selected from among valine, leucine, aspartic acid, glycine, alanine, proline and the like. Most preferably, the linker may be 1 to 5 amino acids selected from among glycine, valine, leucine, aspartic acid and the like, in view of the ease of genetic engineering. In an example of the present invention, a fusion protein was prepared by linking the C-terminus of the skin-penetrating peptide to the N-terminus of a physiologically active protein by a linker consisting of two amino acids (GG). If the fusion protein comprises hGH as a physiologically active protein, it may comprise a peptide represented by the amino acid sequence of SEQ ID NO: 6, and if the physiologically active protein is EGF, the fusion protein may comprise a peptide represented by the amino acid sequence of SEQ ID NO: 7. In addition, if the physiologically active protein is PDGFb, the fusion protein may comprise a peptide represented by the amino acid sequence of SEQ ID NO: 8, and if the physiologically active protein is bFGF, the fusion protein may comprise a peptide represented by the amino acid sequence of SEQ ID NO: 9.

The fusion protein may include a polypeptide having a sequence, one or more amino acid residues of which differ from those of the wild-type amino acid sequence of each domain included therein. Amino acid substitutions that do not generally alter the specific activity thereof are known in the art. The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly. In addition, the fusion protein may include a protein, which has increased stability against heat, changes in pH or the like or increased activity by the mutation or modification of amino acids.

The fusion protein or a polypeptide encoding the fusion protein can be prepared by a chemical peptide synthesis method known in the art. Alternatively, it can be prepared by amplifying a gene encoding the fusion protein by PCR or synthesizing the gene according to a known method, and then cloning the gene into an expression vector, followed by expression.

Thus, the present invention may provide a fusion protein having any one amino acid sequence of SEQ ID NO: 6 to SEQ ID NO: 9, in which the skin-penetrating peptide represented by the amino acid sequence of SEQ ID NO: 1 is linked to the N-terminus of any one amino acid sequence of SEQ ID NO: 2 to SEQ ID NO: 5.

In an example of the present invention, a novel skin-penetrating peptide represented by the amino acid sequence of SEQ ID NO: 1 was discovered by performing a phage display consisting of a combination of elution test methods using a phage library and a transdermal agent. The discovered skin-penetrating peptide was bound to (i) a physiologically active peptide (hGH) represented by the amino acid sequence of SEQ ID NO: 2 to prepare a fusion protein (T-hGH) represented by the amino acid sequence of SEQ ID NO: 6 and (ii) a physiologically active protein (EGF) represented by the amino acid sequence of SEQ ID NO: 3 to prepare a fusion protein (T-EGF) represented by the amino acid sequence of SEQ ID NO: 7. In addition, the skin-penetrating peptide was bound to (iii) a physiologically active protein (PDGHb) represented by the amino acid sequence of SEQ ID NO: 4 to prepare a fusion protein (T-PDGFb) represented by the amino acid sequence of SEQ ID NO: 8 and (iv) a physiologically active protein (PDGHb) represented by the amino acid sequence of SEQ ID NO: 5 to prepare a fusion protein (bFGF) represented by the amino acid sequence of SEQ ID NO: 9. The activities of the prepared fusion proteins were compared with those of physiologically active proteins which were not bound to the skin-penetrating peptide, and as a result, it was shown that the skin penetration and skin retention properties of the fusion proteins were significantly improved (Tables 3-4, 7-8, 11-12 and 15-16) while the expression levels of collagen, elastin, laminin and/or HAS2 (hyaluronan synthase 2) by the fusion proteins were maintained at levels similar to those of the physiologically active proteins (Tables 1-2, 5-6, 9-10 and 13-14).

Accordingly, the fusion protein of the present invention, which comprises the skin-penetrating peptide bound to a physiologically active protein, can significantly enhance the skin penetration and retention of the physiologically active protein while maintaining the effect of the physiologically active protein that increases the synthesis of physiologically active substances, such as collagen, elastin, laminin and/or HAS2 (hyaluronan synthase 2), which show useful effects such as skin wrinkle reduction. Thus, the fusion protein of the present invention is useful as an active ingredient in functional cosmetic compositions and pharmaceutical compositions for external skin use.

In another aspect, the present invention provides a polynucleotide encoding the above-described fusion protein, a fusion protein expression vector comprising the polynucleotide, a transformant comprising the expression vector, and a method of preparing the fusion protein using the transformant.

The polynucleotide can be modified at one or more nucleotides by substitution, deletion, insertion or a combination thereof. The nucleotide sequence of the polynucleotide can be chemically synthesized by a synthesis method widely known in the art, for example, a method described in Engels and Uhlmann, Angew Chem IntEd Engl., 37:73-127, 1988. Examples of the synthesis method include triester, phosphite, phosphoramidite and H-phosphonate methods, PCR and other autoprimer methods as well as oligonucleotide synthesis on solid supports.

As used herein, the term "expression vector" means a recombinant vector capable of expressing a target peptide in a host cell, and refers to a genetic construct including essential regulatory elements operably linked to express a gene insert. The expression vector includes expression regulatory sequences such as an initiation codon, a stop codon, a promoter, an operator and the like. The initiation and stop codons are generally considered as part of a nucleotide sequence encoding the polypeptide and are necessary to be functional in an individual to whom a genetic construct has been administered, and must be in frame with the coding sequence. The promoter of the vector may be constitutive or inducible.

The term "operably linked", as used herein, refers to a functional linkage between a nucleic acid expression control sequence and a second nucleic acid sequence coding for a target protein or RNA in such a manner as to allow general functions. For example, a promoter may be operably linked with a nucleic acid sequence coding for a protein or RNA to influence the expression of the coding sequence. The operable linkage to an expression vector may be prepared using a genetic recombinant technique well known in the art, and site-specific DNA cleavage and ligation may be carried out using enzymes generally known in the art.

Also, the expression vector may include signal sequences for discharge of the fusion polypeptide in order to promote the isolation of protein from a cell culture. Specific initiation signals may also be required for efficient translation of nucleic acid sequences. These signals include the ATG initiation codon and adjacent sequences. In some cases, exogenous translational control signals, including the ATG initiation codon, should be provided. These exogenous translational control signals and initiation codons can be of a variety of origins, both natural and synthetic. The efficiency of expression may be enhanced by the inclusion of appropriate transcription enhancer elements and transcription terminators.

In addition, the expression vector may further comprise a protein tag that may optionally be removed using endopeptidase in order to facilitate the detection of the fusion protein.

As used herein, the term "tag" refers to a molecule which exhibits a quantifiable activity or characteristic. Examples of the tag may include fluorescent molecules including chemical fluorescers such as fluorescein, and polypeptide fluorescers such as green fluorescent protein (GFP) and related proteins, and epitope tags such as a Myc tag, a Flag tag, a His tag, a leucine tag, an IgG tag, and a streptavidin tag. If an epitope tag is used, it is a peptide tag having 6 or more amino acid residues, and preferably about 8 to 50 amino acid residues.

In the present invention, the expression vector may comprise a nucleotide sequence encoding the fusion protein of the present invention. The vector that is used in the present invention is not specifically limited, as long as it makes it possible to prepare the fusion protein of the present invention. Preferably, the vector may be plasmid DNA or phage DNA. More preferably, the vector may be a commercial plasmid (pUC18, pBAD, pIDTSAMRT-AMP, etc.), an *E. coli*-derived plasmid (pYG601BR322, pBR325, pUC118, pUC119, etc.), a *Bacillus subtilis*-derived plasmid (pUB110, pTP5, etc.), a yeast-derived plasmid (YEp13, YEp24, YCp50, etc.), a phage DNA (Charon4A, Charon21A, EMBL3, EMBL4, λgt10, λgt11, λZAP, etc.), an animal virus vector (retrovirus, adenovirus, vaccinia virus, etc.), an insect virus (baculovirus, etc.), or the like. For the expression vector, a host cell most suitable for the intended use is preferably selected and used, because the expression level and modification of protein vary depending on the kind of host cell.

The transformant according to the present invention is constructed by the expression vector of the present invention into a host and can be used to express the polynucleotide contained in the expression vector to thereby prepare the fusion protein of the present invention. The transformation can be performed by various methods. Any transformation method may be used in the present invention, as long as it can prepare the fusion protein of the present invention that shows the effect of increasing various cell activities to high levels. Examples of the transformation method include, but are not limited to, $CaCl_2$ precipitation, the Hanahan method using DMSO (dimethyl sulfoxide) as a reducing agent on the basis of the $CaCl_2$ precipitation, electroporation, calcium phosphate precipitation, plasma fusion, agitation using silicon carbide fiber, agrobacteria-mediated transformation, PEG-mediated transformation, and PEG-, dextran sulfate-, lipofectamine- or desiccation/inhibition-mediated transformation. Also, the host that is used in the construction of the transformant is not specifically limited, as long as it can prepare the fusion protein of the present invention. Examples of the host include, but are not limited to, bacterial cells such as *E. coli, Streptomyces* and *Salmonella typhimurium* cells; yeast cells suhc as *Saccharomyces cerevisiae*; fungal cells such as *Pichia pastoris*; insect cells such as *Drosophila* S2 and *Spodoptera* Sf9 cells; animal cells such as CHO, COS, NSO, 293, and Bowes melanoma cells; and plant cells.

The transformant can also be used in the method of preparing the fusion protein of the present invention. Specifically, the method of preparing the fusion protein of the present invention may comprise the steps of: (a) culturing the transformant to obtain a culture product; and (b) recovering the fusion protein of the present invention from the culture product.

As used herein, the term "culturing" means a method of allowing a microorganism to grow under artificially control environmental conditions. In the present invention, the method of culturing the transformant can be performed using a method widely known in the art. Specifically, the culturing can be performed by a batch process, a fed-batch process or a fed batch or a continuous process such as a repeated fed batch process. In addition, any culturing process may be used in the present invention, as long as it can express the fusion protein of the present invention.

The medium that is used in the culturing contains suitable carbon sources, nitrogen sources, amino acids, vitamins and the like and should satisfy the requirements of a specific strain in a suitable manner while adjusting temperature, pH and the like under aerobic conditions. Carbon sources that may be used in the present invention include, in addition to mixed sugars of glucose and xylose as a main carbon source, sugars and carbohydrates such as sucrose, lactose, fructose, maltose, starch and cellulose, oils and fats such as soybean oil, sunflower oil, castor oil and coconut oil, fatty acids such as palmitic acid, stearic acid and linoleic acid, alcohols such as glycerol and ethanol, and organic acids such as acetic acid. These substances may be used alone or in combination. Nitrogen sources that may be used in the present invention include inorganic nitrogen sources such as ammonia, ammonium sulfate, ammonium chloride, ammonium acetate, ammonium carbonate, and ammonium nitrate; amino acids such as glutamic acid, methionine and glutamine; and organic nitrogen sources such as peptone, NZ-amine, corn steep liquor, meat extract, yeast extract, casein hydrolysate, fish meal or its digested product, defatted soybean cake or its digested product, etc. These nitrogen sources may be used alone or in combination. The medium may contain, as phosphorus sources, potassium phosphate monobasic, potassium phosphate dibasic and corresponding sodium-containing salts. Phosphorus sources that may be used in the present invention include potassium dihydrogen phosphate, dipotassium hydrogen phosphate and corresponding sodium-containing salts. In addition, inorganic compounds that may be used in the present invention include sodium chloride, calcium chloride, iron chloride, magnesium sulfate, iron sulfate, manganese sulfate and calcium carbonate. In addition to the above materials, essential growth materials such as amino acids and vitamins may be used in the present invention.

Further, the culture medium may contain suitable precursors. The above-described materials may be added to the medium in a batch, fed-batch or continuous manner, but are not limited thereto. The pH of the medium can be adjusted using basic compounds such as sodium hydroxide, potassium hydroxide or ammonia, or acidic compounds such as phosphoric acid or sulfuric acid.

In addition, the formation of bubbles can be inhibited by using an antiforming agent such as fatty acid polyglycol ester. In order to maintain an aerobic state, oxygen or oxygen-containing gas (e.g. air) can be injected. The temperature of culture product is generally 27 to 37° C., preferably 30 to 35° C. Culture is continued until the desired level of the fusion protein production will be obtained. This is achieved within 10 to 100 hours.

In addition, the step of recovering the fusion protein from the culture product may be performed by a method known in the art. The recovering method is not specifically limited, as long as it can recover the fusion protein of the present invention. Preferred examples of the recovering method include centrifugation, filtration, extraction, spray, drying, evaporation, precipitation, crystallization, electrophoresis, fractional dissolution (e.g., ammonium sulfate precipitation), chromatography (e.g., ion exchange, affinity, hydrophobic and size exclusion) and the like.

In still another aspect, the present invention provides a composition for improving skin conditions, which comprises the fusion protein as an active ingredient, and a method for improving skin conditions, which comprises transdermally administering the composition.

As described above, the fusion protein according to the present invention can significantly enhance the skin penetration and skin retention of physiologically active proteins such as hGF, EGF, PDGFb and bFGF while maintaining or enhancing the production of collagen, elastin, laminin and/or HAS2 by the physiologically active proteins. Thus, the fusion protein of the present invention can be used as an active ingredient in a cosmetic composition which can improve skin conditions.

As used herein, the term "improving skin conditions" generally means the process or effect of treating, alleviating or relieving skin damage caused by intrinsic or extrinsic factors. For the purpose of the present invention, it can be understood that the term "improving skin conditions" means effects such as the promotion of synthesis of collagen, elastin, laminin and/or HAS2 in skin cells, and thus wrinkle reduction, skin moisturization, skin whitening, skin elasticity maintenance and/or enhancement, wound healing, anti-aging, dermatitis relief or alleviation, which can be induced by applying the fusion protein of the present invention to the skin.

The fusion protein is preferably contained in an amount of 0.0001-50 wt % based on the total eight of the cosmetic composition. If the content of the fusion protein is less than 0.0001 wt % based on the total weight of the cosmetic composition, it cannot show the effect of improving skin conditions, and if the content of the fusion protein is more than 50 wt %, it will make the formulation unstable.

Meanwhile, the cosmetic composition according to the present invention may further comprise an additive. The additive may be one or more selected from among, for example, oil, water, a surfactant, a moisturizing agent, a lower alcohol, a sterilizing agent, an antioxidant, a thickener, a chelating agent, a pigment, a preservative and a fragrance, but is not limited thereto. Such additives may be used in suitable amounts selected to suit the desired purpose.

In still another aspect, the present invention provides a functional cosmetic product comprising the composition for improving skin conditions.

As used herein, the terms "functional cosmetic product", "cosmedical product" or "cosmeceutical" refer to a cosmetic product that has the special therapeutic effects of medical drugs, and thus shows special functionalities such as physiologically active effects, unlike general cosmetic products. The terms include a product that assists in skin whitening, a product that assists in skin wrinkle reduction, and a cosmetic product that assists in tanning the skin or protecting the skin from UV rays.

A suitable carrier that is used in the manufacture of general skin cosmetic products may be added to the cosmetic composition of the present invention to manufacture a functional cosmetic product. The carrier that is used in the present invention is not specifically limited, but is preferably one or a mixture of two or more selected from among oil, water, a surfactant, a moisturizing agent, a lower alcohol, a thickener, a chelating agent, a pigment, a preservative, a fragrance and the like.

The functional cosmetic product of the present invention shows the effect of improving skin conditions by promoting the synthesis of collagen, elastin, laminin and/or HAS2. The formulation of the functional cosmetic product is not specifically limited, but may be, for example, a solution, emulsion, suspension, paste, cream, lotion, gel, powder, spray, surfactant-containing cleansing cake, oil, soap, liquid cleanser, bath soak, foundation, makeup base, essence, foam, pack, sun screen cream or sun oil formulation. Preferably, the formulation may be a skin external ointment, skin softener, skin lotion, nourishing cream, massage cream, essence, pack, emulsion or oil gel formulation. A carrier for the functional cosmetic product may be selected depending on the formulation of the functional cosmetic product.

For example, if the formulation of the cosmetic product is an ointment, paste, cream or gel formulation, it may comprise, as a carrier component, one or a mixture of two or more selected from among wax, paraffin, starch, tragacanth gum, cellulose derivatives, polyethylene glycol, silicone, bentonite, silica, talc, zinc oxide and the like; if the formulation is a powder or spray formulation, it may comprise, as a carrier component, one or a mixture of two or more selected from among lactose, talc, silica, aluminum hydroxide, calcium silicate, polyamide powder, chlorofluorohydrocarbon, propane/butane, dimethyl ether and the like; if the formulation is a solution or emulsion formulation, it may comprise, as a carrier component, one or a mixture of two or more selected from among water, ethanol, isopropanol, ethyl carbonate, ethyl acetate, benzyl alcohol, benzyl benzoate, propylene glycol, 1,3-butyl glycol oil, cotton seed oil, peanut oil, corn germ oil, olive oil, castor oil, sesame oil, glycerol, aliphatic ester, polyethylene glycol, and fatty acid ester of sorbitan; if the formulation is a suspension, it may comprise, as a carrier component, one or a mixture of two or more selected from among water, ethanol, propylene glycol, ethoxylated isostearyl alcohol, polyoxyethylene sorbitol ester, polyoxyethylene sorbitan ester, microcrystalline cellulose, aluminum methahydroxide, bentonite, agar, tragacanth gum and the like; if the formulation is a cosmetic soap, it may comprise, as a carrier component, one or a mixture of two or more selected from among alkali metal salts of fatty acids, hemiester salts of fatty acids, fatty acid protein hydrolysate, isethionate, lanolin derivatives, aliphatic alcohols, vegetable oils, glycerol, sugars and the like.

In specific embodiments, a skin external ointment may contain, in addition to the fusion protein of the present invention, 50-97 wt % of Vaseline and 0.1-5 wt % of polyoxyethyleneoleyl-ether phosphate; a skin softener may contain, in addition to the fusion protein of the present invention, 1-10 wt % of a polyhydric alcohol such as propylene glycol or glycerin and 0.05-2 wt % of a surfactant such as polyethyleneoleylether or polyoxyethylene hydrogenated castor oil; skin lotion or nourishing cream may contain, in addition to the fusion protein of the present invention, 5-20 wt % of oils such as squalane, Vaseline or octyldodecanol and 3-15 wt % of wax components such as cetanol, stearyl alcohol or beeswax; essence may contain, in addition to the fusion protein of the present invention, 5-30 wt % of a polyhydric alcohol such as glycerin or propylene glycol; massage cream may contain, in addition to the fusion protein of the present invention, 30-70 wt % of liquid paraffin, Vaseline or isononyl isononanoate; a pack may be prepared as a peel-off pack containing, in addition to the fusion protein of the present invention, 5-20 wt % of polyvinyl alcohol, or a wash-off pack containing, in addition to a general emulsion-type cosmetic composition, 5-30 wt % of kaolin, talc, zinc oxide or titanium dioxide.

In still another aspect, the present invention provides a pharmaceutical composition for external skin use, which comprises the fusion protein of the present invention. As is known in the art, the human growth hormone functions to stimulate the differentiation of growth plate chondrocytes to promote growth, and if the in vivo synthesis and secretion of the growth hormone is deficient, short stature, an increase in the risk of cardiovascular diseases, decreases in muscle and bone densities, etc., may occur. Because it was found that the fusion protein according to the present invention can maintain or enhance the effect of the human growth factor (hGH), the fusion protein can improve the effects of hGH, including the promotion of cell proliferation, wound healing, the treatment of neurodegenerative diseases, ischemic neurologic disease, the treatment of nerve injury disease, and the treatment of arthritis. Thus, the fusion protein of the present invention may be used as an active ingredient in a pharmaceutical composition for external skin use which shows the effects of treating or alleviating the above diseases or conditions.

It is known that epidermal growth factor mainly functions to stimulate the regeneration and differentiation of intestinal mucosa, corneal tissue and lung tissue, thereby promoting epidermal proliferation, blood vessel formation and would healing and inhibiting gastric acid secretion. Because it was found that the fusion protein of the present invention can maintain or enhance the effects of the EGF, the fusion protein can improve the effects of EFG on the treatment of skin aging, atopy, dermatitis, corneal disease stomach ulcer, and thus can be used as an active ingredient in a pharmaceutical composition for external skin use which shows the effects of treating or alleviating the above diseases or conditions.

It is known that platelet-derived growth factor-b subunit shows effects on the promotion of cell proliferation, wounding healing and the treatment of neurodegenerative diseases, ischemic neurologic disease, nerve injury disease, arthritis and the like. It was found that the fusion protein of the present invention can improve the effects of PDGFb. Accordingly, the fusion protein can improve the effects of PDGFb on the promotion of cell proliferation, wounding healing and the treatment of neurodegenerative diseases, ischemic neurologic disease, nerve injury disease, arthritis and the like, and thus can be used as an active ingredient in a pharmaceutical composition for external skin use which shows the effects of treating or alleviating the above diseases or conditions.

It is known that basic fibroblast growth factor shows effects on the treatment of skin aging, skin scars and skin trauma, the improvement of skin conditions, the treatment of periodontal disease, and the promotion of cell proliferation, vascular regeneration and endothelial cell growth, etc. It was found that the fusion protein of the present invention can improve the effects of bFGF. Accordingly, the fusion protein can improve the effects of bFGF on the treatment of skin aging, skin scar and skin trauma, the improvement of skin conditions, the treatment of periodontal disease, and the promotion of cell proliferation, vascular regeneration and endothelial cell growth, etc., and thus can be used as an active ingredient in a pharmaceutical composition for external skin use which shows the effects of treating or alleviating the above diseases or conditions.

As used herein, term "composition for external skin application" refers to solid, semi-solid or liquid medicines for external use, prepared by adding an active ingredient to various bases such as oils, Vaseline, lanoline and glycerol so that it can be easily applied to the skin. The formulation of the composition for external skin use is not specifically limited, but is preferably a powder, gel, ointment, cream, liquid or aerosol formulation.

For the purpose of the present invention, the composition for external skin use can be understood to be a preparation that comprises the fusion protein of the present invention and a suitable base as a carrier for external skin use, but is not limited thereto.

The pharmaceutical composition of the present invention may further contain a suitable carrier, excipient and diluent which is commonly used in the preparation of pharmaceutical compositions. Herein, the content of the fusion protein of the composition is not specifically limited, but may be 0.01-50.0 wt %, and preferably 5-20 wt %, based on the total weight of the composition.

The pharmaceutical composition may have a formulation selected from the group consisting of any one or more of tablets, pills, powders, granules, capsules, suspensions, solutions, emulsions, syrups, sterile aqueous solutions, non-aqueous solvents, suspending agents, freeze-dried preparations, and suppositories and may be formulated for oral or parenteral administration. The composition of the present invention may be formulated with commonly used diluents or excipients, such as fillers, extenders, binders, wetting agents, disintegrants, surfactants, etc. Solid formulations for oral administration include tablets, pills, powders, granules, capsules and the like, and such solid formulations comprise, in addition to the composition, at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions, and syrup, and may contain various excipients, for example, wetting agents, flavoring agents, aromatics and preservatives, in addition to water and liquid paraffin, which are frequently used simple diluents. Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, and the like can be used. As the base of the suppositories, witepsol, Macrogol, Tween 61, cacao butter, laurin fat, glycerogelatin and the like can be used.

The composition of the present invention may be administered in a pharmaceutically effective amount.

As used herein, the term "pharmaceutically effective amount" refers to an amount sufficient to treat diseases, at a reasonable benefit/risk ratio applicable to any medical treatment. The effective dosage level of the composition may be determined depending on the subject's type, the disease severity, the subject's age and sex, the type of infected virus, the activity of the drug, sensitivity to the drug, the time of administration, the route of administration, excretion rate, the duration of treatment, drugs used in combination with the composition, and other factors known in the medical field. The pharmaceutical composition of the present invention may be administered individually or in combination with other therapeutic agents, and may be administered sequentially or simultaneously with conventional therapeutic agents. The composition can be administered in a single or multiple dosage form. It is important to administer the composition in the minimum amount that can exhibit the maximum effect without causing side effects, in view of all the above-described factors, and this amount can be easily determined by a person skilled in the art.

The preferred dose of the composition of the present invention varies depending on the patient's sex and weight, the severity of the disease, the type of drug, and the route and period of administration. The suitable total daily dose can be can be determined by the physician, but may generally be 0.001-1000 mg/kg, preferably 0.05 to 200 mg/kg, and more preferably 0.1 to 100 mg/kg, which can be administered once a day or in divided doses. A subject to which the composition is to be administered is not specifically limited. Examples of the subject include non-human animals such as monkeys, dogs, cats, rabbits, guinea pigs, rats, mice, cattle, sheep, pigs or goats, and humans. The composition of the present invention may be administered by any method known in the art. For example, the composition may be administered transdermally by topical application, but is not limited thereto.

Hereinafter, the present invention will be described in further detail with reference to examples. It is to be understood, however, that these examples are for illustrative purposes only and are not intended to limit the scope of the present invention.

EXAMPLE 1

Selection of Skin-penetrating Peptide

In order to select a skin-penetrating peptide, a phage display method consisting of a combination of elution test methods using a phage library and a transdermal agent was performed.

First, $10^9$ phages derived from Ph.D-12 phage library kit (New England Biolab) were added to 500 μl of 1% BSA-containing TBS (50 mM Tris pH 7.5, 150 mM NaCl) solution to prepare a phage solution.

Then, the porcine skin (0.7 mm thickness, Medikinetics) was placed between the upper and lower ends of Franz glass cell (Standard diameter: 9 mm, Receiver: 5 ml, Permgear), and the phage solution was added thereto and allowed to react for 16 hours. Then, the phages that penetrate the porcine skin to reach a receiver at the lower end were collected and amplified.

The amplification was performed using *E. coli* ER2738 (New England Biolab) as a host cell. Specifically, 5 ml and of the phage solution was added to an *E. coli* ER2738 strain shake-cultured in 25 ml and of LB medium and cultured for 4 hours. Then, the culture was centrifuged at 8,000 G, and the supernatant containing the phage fraction was collected. The supernatant was treated and reacted with 6 ml and of precipitation buffer (20% PEG6000, 2.5M NaCl) to precipitate the phages, and the reaction solution was centrifuged at 8,000 G to precipitate the phages. The precipitate was suspended in TBS solution to obtain an amplified phage solution.

The above-described process of adding phages to the porcine skin, collecting the phages that penetrated the skin and amplifying the collected phages was defined as round 1. The phages amplified in round 1 were subjected to round 2, whereby phages showing good skin penetration were selected in a competitive manner. A total of 3 rounds were performed.

In order to determine the sequence of a peptide contained in the phage obtained by performing the above-described 3 rounds, TBS solution containing the phage was added to an *E. coli* ER2738 strain and suspended, and TOP agar was added to and mixed with the suspension, and the mixture was added to LB/X-gal/IPTG plate medium and solidified. The solidified medium was incubated for 16 hours, and then a blue colony was selected. The strain derived from the selected colony was cultured, and DNA was collected therefrom. Then, the nucleotide sequence of the DNA derived from the phage was analyzed, thereby determining the amino acid sequence (SEQ ID NO: 1) of the peptide showing the property of penetrating the porcine skin.

EXAMPLE 2

Preparation of Fusion Protein

EXAMPLE 2-1

Preparation of Fusion Protein Comprising Skin-penetrating Peptide and Human Growth Hormone (hGH)

The C-terminus of the skin-penetrating peptide having the amino acid sequence of SEQ ID NO: 1, obtained in Example 1, was linked to the N-terminus of a human growth hormone (hGH) having the amino acid sequence of SEQ ID NO: 2 by a linker consisting of two amino acids (GG), thereby preparing the fusion protein T-hGH (SEQ ID NO: 6).

Specifically, a polynucleotide encoding the amino acid sequence of SEQ ID NO: 1 and a polynucleotide encoding the amino acid sequence of SEQ ID NO: 2 were synthesized and linked to each other by a nucleotide sequence encoding two amino acids (GG), thereby constructing a polynucleotide sequence encoding the amino acid sequence of SEQ ID NO: 6. Meanwhile, a polynucleotide encoding the cleavage site DDDDK (Asp-Asp-Asp-Asp-Lys) (SEQ ID NO:10) that can be cleaved by enterokinase was synthesized and linked to the 5'-terminal end of the above-constructed polynucleotide encoding the amino acid sequence of SEQ ID NO: 6, thereby obtaining a final polynucleotide encoding the fusion protein composed of the enterokinase cleavage site, the skin-penetrating peptide and the hGH. The obtained polynucleotide was introduced into a GST expression vector, thereby constructing an expression vector.

The constructed expression vector was introduced into *E. coli* to obtain a transformant. The obtained transformant was lysed to obtain a cell lysate. The obtained cell lysate was applied to a GST affinity column to recover a fusion protein composed of the GST, the enterokinase cleavage site, the skin-penetrating peptide and the hGH. The recovered fusion protein was treated with enterokinase to remove the GST portion, and then the remaining fusion protein was subjected to GPC column chromatography, thereby preparing the fusion protein T-hGH (SEQ ID NO: 6) composed of the skin-penetrating peptide and the hGH.

EXAMPLE 2-2

Preparation of Fusion Protein Comprising Skin-penetrating Peptide and Epidermal Growth Factor (EGF)

In the same manner as described in Example 2-1 above, the C-terminus of the skin-penetrating peptide having the amino acid sequence of SEQ ID NO: 1, obtained in Example 1, was linked to the N-terminus of an epidermal growth factor (EGF) having the amino acid sequence of SEQ ID NO: 3 by a linker consisting of two amino acids (GG), thereby preparing the fusion protein T-EGF (SEQ ID NO: 7).

EXAMPLE 2-3

Preparation of Fusion Protein Comprising Skin-penetrating Peptide and Platelet-derived Growth Factor-b Subunit In the same manner as described in Example 2-1 above, the C-terminus of the skin-penetrating peptide having the amino acid sequence of SEQ ID NO: 1, obtained in Example 1, was linked to the N-terminus of a platelet-derived growth factor-b subunit (PDGFb) having the amino acid sequence of SEQ ID NO: 4 by a linker consisting of two amino acids (GG), thereby preparing the fusion protein T-PDGFb (SEQ ID NO: 8).

EXAMPLE 2-4

Preparation of Fusion Protein Comprising Skin-penetrating Peptide and Fibroblast Growth Factor In the same manner as described in Example 2-1 above, the C-terminus of the skin-penetrating peptide having the amino acid sequence of SEQ ID NO: 1, obtained in Example 1, was linked to the N-terminus of a fibroblast growth factor having the amino acid sequence of SEQ ID NO: 5 by a linker consisting of two amino acids (GG), thereby preparing the fusion protein T-bFGF (SEQ ID NO: 9).

EXAMPLE 3

Verification of Effects of Fusion Proteins

EXAMPLE 3-1

Verification of Effects of T-hGH

EXAMPLE 3-1-1

Verification of Effect on Collagen Expression

The effects of T-hGH (synthesized in Example 2-1) and hGH on the production of collagen and elastin were verified.

Specifically, fibroblasts were inoculated into a 6-well plate containing DMEM medium and were cultured for 24 hours to obtain a culture product showing a saturation degree of 70-80%. Various concentrations (10, 100 and 1000 ng/ml) of T-hGH or hGH were added to the culture product and further cultured for 16 hours. After completion of the culture, the cultured cells were washed with PBS, and total RNA was isolated from the cells using an RNAeasy kit. The isolated total RNA was subjected to reverse transcription (RT)-PCR to obtain cDNA, and the obtained cDNA was subjected to real-time PCR, thereby quantitatively determining the expression level of collagen. As a control group, fibroblasts cultured without treatment with T-hGH or hGH were used, and as an internal control, GAP3DH mRNA was used (see Table 1).

TABLE 1

Effect of fusion protein on collagen expression

| Treated protein | Concentration of protein | Expression level (%) |
|---|---|---|
| Control | — | 100 ± 21 |
| hGH | 10 ng/ml | 118 ± 16 |
|  | 100 ng/ml | 124 ± 25 |
|  | 1000 ng/ml | 312 ± 31 |
| T-hGH | 10 ng/ml | 98 ± 23 |
|  | 100 ng/ml | 150 ± 32 |
|  | 1000 ng/ml | 290 ± 16 |

As can be seen in Table 1 above, when the cells were treated with hGH or T-hGH, the expression level of collagen in the cells increased compared to that in the control group, and the expression level of collagen in the cells treated with T-hGH was maintained at a level similar to that in the cells treated with hGH. Particularly, at a protein concentration of 100 ng/ml, the expression level of collagen was higher in the T-hGH-treated cells than in the hGH-treated cells.

Thus, it can be seen that, when the fusion protein of the present invention is used, collagen can be synthesized at a level similar to or higher than when hGH is used alone.

EXAMPLE 3-1-2

Verification of Effect on Elastin Expression

The effect of T-hGH or hGH on the expression of elastin was verified in the same manner as described in Example 3-1-1, except that the expression level of elastin in place of collagen was quantitatively analyzed (see Table 2).

TABLE 2

Effect of fusion protein on elastin expression

| Treated protein | Concentration of protein | Expression level (%) |
|---|---|---|
| Control | — | 100 ± 14 |
| hGH | 10 ng/ml | 112 ± 4 |
|  | 100 ng/ml | 200 ± 11 |
|  | 1000 ng/ml | 330 ± 23 |
| T-hGH | 10 ng/ml | 97 ± 16 |
|  | 100 ng/ml | 190 ± 19 |
|  | 1000 ng/ml | 318 ± 21 |

As can be seen in Table 2 above, when the cells were treated with hGH or T-hGH, the expression of elastin in the cells increased compared to that in the control group, and the expression level of elastin in the cells treated with T-hGH— was maintained at a level similar to that in the cells treated with hGH.

EXAMPLE 3-1-3

Verification of Skin Penetration

The skin penetration of the fusion protein was verified using Franz glass cell (standard diameter: 9 mm, receiver: 5 ml, Permegear).

Specifically, the porcine skin (0.7 mm thickness, Medikinetics) was placed between the upper and lower ends of the glass cell, and TBS (50 mM Tris pH 7.5, 150 mM NaCl) containing 1% BSA and 0.01% Tween 20 was prepared. Then, 500 μl of the TBS was added to the upper end (donor chamber) of the glass cell, and 5 ml and of the TBS was added to the lower end (receiver chamber) of the glass cell. Then, 200 μg of hGH or T-hGH was added to the upper end of the cell and allowed to react for 16 hours, after which the concentration of hGH and T-hGH at the lower end was quantitatively analyzed using a human-hGH ELISA kit (DGH00, R&D system), and the content of T-hGH relative to the content of hGH was calculated as penetration rate (see Table 3).

TABLE 3

Skin penetration rate (%) of fusion protein

| Treated protein | Penetration rate (%) |
|---|---|
| hGH | 100 ± 23 |
| T-hGH | 490 ± 31 |

As can be seen in Table 3 above, the skin penetration rate of T-hGH was about 5 times higher than that of hGH.

Thus, it can be seen that the use of the fusion protein of the present invention significantly increases the skin penetration rate of hGH.

EXAMPLE 3-1-4

Verification of Skin Retention

The skin retention of the fusion protein was verified using Franz glass cell (standard diameter: 9 mm, receiver: 5 ml, Permegear).

Specifically, the porcine skin (0.7 mm thickness, Medikinetics) was placed between the upper and lower ends of the glass cell, and TBS (50 mM Tris pH 7.5, 150 mM NaCl) containing 1% BSA and 0.01% Tween 20 was prepared. Then, 500 μl of the TBS was added to the upper end of the glass cell, and 5 ml and of the TBS was added to the lower end of the glass cell. 200 μg of each of hGH and T-hGH was added to the donor chamber of the Franz cell system containing the porcine skin, and the porcine skin tissue was disrupted and analyzed using an ELISA kit to measure the amount of hGH present in the porcine skin (see Table 4).

TABLE 4

Skin retention of fusion protein

| Treated protein | Retention (%) |
|---|---|
| hGH | 100 ± 35 |
| T-hGH | 11000 ± 1300 |

As can be seen in Table 4 above, the skin retention of T-hGH was about 110 times higher than that of hGH.

Thus, it can be seen that the use of the fusion protein of the present invention significantly increases the skin retention rate of hGH.

EXAMPLE 3-2

Verification of Effects of T-EGF Fusion Protein

EXAMPLE 3-2-1

Verification of Effect on Expression of Laminin

The effects of T-EGH (synthesized in Example 2-2) and hGH on the production of laminin and HAS2 were verified.

Specifically, Hacat cells were inoculated into a 6-well plate containing DMEM medium and were cultured for 24 hours to obtain a culture product showing a saturation degree of 70-80%. Next, the medium was replaced with serum-free DMEM medium, and then various concentrations (10, 10 and 100 ng/ml) of T-EGF or EGF were added to the culture product and further cultured for 16 hours. After completion of the culture, the cultured cells were washed with PBS, and total RNA was isolated from the cells using an RNAeasy kit. The isolated total RNA was subjected to RT-PCR to obtain cDNA, and the obtained cDNA was subjected to real-time PCR, thereby quantitatively determining the expression level of laminin. As a control group, Hacat cells cultured without treatment with T-EGF or EGF were used, and as an internal control, GAP3DH mRNA was used (see Table 5).

TABLE 5

Effect of fusion on expression of laminin

| Treated protein | Concentration of protein | Expression level (%) |
|---|---|---|
| Control | — | 100 ± 13 |
| EGF | 1 ng/ml | 98 ± 11 |
|  | 10 ng/ml | 250 ± 25 |
|  | 100 ng/ml | 520 ± 31 |
| T-EGF | 1 ng/ml | 110 ± 19 |
|  | 10 ng/ml | 270 ± 23 |
|  | 100 ng/ml | 510 ± 32 |

As can be seen in Table 5 above, when the cells were treated with EGF or T-EGF, the expression level of laminin increased in a concentration-dependent manner compared to that in the control. Also, the expression level of laminin in the T-EGF-treated cells was maintained at a level similar to or higher than that in the cells treated with EGF.

Thus, it can be seen that, when the fusion protein of the present invention is used, laminin can be synthesized at a level similar to or higher than when EGF is used alone.

EXAMPLE 3-2-2

Verification of Effect on Expression of HAS2 (Hyaluronan Synthase 2)

The effect of T-EGF or EGF on the expression of HAS2 was verified in the same manner as described in Example 3-2-1, except that the expression level of HAS2 in place of laminin was quantitatively analyzed (see Table 6).

TABLE 6

Effect of fusion protein on expression of HAS2

| Treated protein | Concentration of protein | Expression level (%) |
|---|---|---|
| Control | — | 100 ± 19 |
| EGF | 1 ng/ml | 110 ± 9 |
|  | 10 ng/ml | 200 ± 14 |
|  | 100 ng/ml | 550 ± 23 |
| T-EGF | 1 ng/ml | 90 ± 11 |
|  | 10 ng/ml | 190 ± 19 |
|  | 100 ng/ml | 580 ± 39 |

As can be seen in Table 6 above, when the cells treated with EGF or T-EGF, the expression level of HAS2 generally increased compared to that in the control, like the case of laminin. Particularly, the expression level of HAS2 in the T-EGF-treated cells was similar to or higher than that in the cells treated with EGF.

EXAMPLE 3-2-3

Verification of Skin Penetration

The skin penetration of the fusion protein was verified using Franz glass cell (standard diameter: 9 mm, receiver: 5 ml, Permegear).

Specifically, the porcine skin (0.7 mm thickness, Medikinetics) was placed between the upper and lower ends of the glass cell, and TBS (50 mM Tris pH 7.5, 150 mM NaCl) containing 1% BSA and 0.01% Tween 20 was prepared. Then, 500 µl of the TBS was added to the upper end (donor chamber) of the glass cell, and 5 ml and of the TBS was added to the lower end (receiver chamber) of the glass cell. Then, 200 µg of EGF or T-EGF was added to the upper end of the cell and allowed to react for 16 hours, after which the concentration of hGH and T-hGH at the lower end was quantitatively analyzed using a human-EGH ELISA kit (DGH00, R&D system), and the content of T-EGF relative to the content of EGH was calculated as permeation rate (see Table 7).

TABLE 7

Skin penetration of fusion protein

| Treated protein | Penetration rate (%) |
|---|---|
| EGF | 100 ± 13 |
| T-EGF | 280 ± 31 |

As can be seen in Table 7 above, the skin penetration rate of T-EGF was about 3 times higher than that of EGF.

Thus, it can be seen that the use of the fusion protein of the present invention significantly increases the skin penetration rate of EGF.

EXAMPLE 3-2-4

Verification of Skin Retention

The skin retention of the fusion protein was verified using Franz glass cell (standard diameter: 9 mm, receiver: 5 ml, Permegear).

Specifically, the porcine skin (0.7 mm thickness, Medikinetics) was placed between the upper and lower ends of the glass cell, and TBS (50 mM Tris pH 7.5, 150 mM NaCl) containing 1% BSA and 0.01% Tween 20 was prepared. Then, 500 µl of the TBS was added to the upper end of the glass cell, and 5 ml and of the TBS was added to the lower end of the glass cell. 200 µg of each of conventional EGH and T-EGH was added to the donor chamber of the Franz cell system containing the porcine skin, and the porcine skin tissue was disrupted and analyzed using an ELISA kit to measure the amount of EGH present in the porcine skin (see Table 8).

TABLE 8

Skin retention of fusion protein

| Treated protein | Retention (%) |
|---|---|
| EGF | 100 ± 25 |
| T-EGF | 10200 ± 1300 |

As can be seen in Table 8 above, the skin retention of T-EGH was about 100 times higher than that of EGH.

Thus, it can be seen that the use of the fusion protein of the present invention significantly increases the skin retention rate of EGH.

EXAMPLE 3-3

Verification of Effects of T-PDGFb Fusion Protein

EXAMPLE 3-3-1

Verification of Effect on Collagen Expression

The effects of T-PDGFb (synthesized in Example 2-3) and PDGFb on the production of collagen and elastin were verified.

Specifically, fibroblasts were inoculated into a 6-well plate containing DMEM medium and were cultured for 24 hours to obtain a culture product showing a saturation degree of 70-80%. Various concentrations (1, 10 and 100 ng/ml) of T-PDGFb or PDGFb were added to the culture product and further cultured for 16 hours. After completion of the culture, the cultured cells were washed with PBS, and total RNA was isolated from the cells using an RNAeasy kit. The isolated total RNA was subjected to RT-PCR to obtain cDNA, and the obtained cDNA was subjected to real-time PCR, thereby quantitatively determining the expression level of collagen. As a control group, fibroblasts cultured without treatment with T-PDGFb or PDGFb were used, and as an internal control, GAP3DH mRNA was used (see Table 9).

TABLE 9

Effect of fusion protein on collagen expression

| Treated protein | Concentration of protein | Expression level (%) |
|---|---|---|
| Control | — | 100 ± 11 |
| PDGFb | 1 ng/ml | 190 ± 13 |
|  | 10 ng/ml | 324 ± 35 |
|  | 100 ng/ml | 630 ± 35 |
| T-PDGFb | 1 ng/ml | 212 ± 31 |
|  | 10 ng/ml | 360 ± 26 |
|  | 100 ng/ml | 670 ± 36 |

As can be seen in Table 9, when the cells were treated with PDGFb or T-PDGFb, the expression level of collagen in the cells increased compared to that in the control group. Also, the expression level of collagen in the treated cells treated with T-PDGFb was higher than that in the cells treated with PDGFb.

Thus, it can be seen that the use of the fusion protein of the present invention can increase the expression level of collagen compared to the use of PDGFb alone.

EXAMPLE 3-3-2

Verification of Effect on Elastin Expression

The effect of T-PDGFb or PDGFb on the expression of elastin was verified in the same manner as described in Example 3-3-1, except that the expression level of elastin in place of collagen was quantitatively analyzed (see Table 10).

TABLE 10

Effect of fusion protein on elastin expression

| Treated protein | Concentration of protein | Expression level (%) |
|---|---|---|
| Control | — | 100 ± 12 |
| PDGFb | 1 ng/ml | 180 ± 11 |
|  | 10 ng/ml | 322 ± 19 |
| T-PDGFb | 1 ng/ml | 192 ± 26 |
|  | 10 ng/ml | 370 ± 34 |

As can be seen in Table 10, when the cells were treated with PDGFb or T-PDGFb, the expression level of elastin in the cells increased compared to that in the control group. Also, the expression level of elastin in the treated cells treated with T-PDGFb was higher than that in the cells treated with PDGFb.

Thus, it can be seen that the use of the fusion protein of the present invention can increase the expression level of elastin compared to the use of PDGFb alone.

EXAMPLE 3-3-3

Verification of Skin Penetration

The skin penetration of the fusion protein was verified using Franz glass cell (standard diameter: 9 mm, receiver: 5 ml, Permegear).

Specifically, the porcine skin (0.7 mm thickness, Medikinetics) was placed between the upper and lower ends of the glass cell, and TBS (50 mM Tris pH 7.5, 150 mM NaCl) containing 1% BSA and 0.01% Tween 20 was prepared. Then, 500 μl of the TBS was added to the upper end (donor chamber) of the glass cell, and 5 ml and of the TBS was added to the lower end (receiver chamber) of the glass cell. Then, 200 μg of PDGFb or T-PDGFb was added to the upper end of the cell and allowed to react for 16 hours, after which the concentration of PDGFb or T-PDGFb at the lower end was quantitatively analyzed using a human PDGF-BB ELISA (DGH00, R&D system), and the content of T-PDGFb relative to the content of PDGFb was calculated as penetration rate (see Table 11).

TABLE 11

Skin penetration rate (%) of fusion protein

| Treated protein | Penetration (%) |
|---|---|
| PDGFb | 100 ± 25 |
| T-PDGFb | 490 ± 38 |

As can be seen in Table 11 above, the skin penetration rate of T-PDGFb was about 5 times higher than that of PDGFb.

Thus, it can be seen that the use of the fusion protein of the present invention significantly increases the skin penetration rate of PDGFb.

EXAMPLE 3-3-4

Verification of Skin Retention

The skin retention of the fusion protein was verified using Franz glass cell (standard diameter: 9 mm, receiver: 5 ml, Permegear).

Specifically, the porcine skin (0.7 mm thickness, Medikinetics) was placed between the upper and lower ends of the glass cell, and TBS (50 mM Tris pH 7.5, 150 mM NaCl) containing 1% BSA and 0.01% Tween 20 was prepared. Then, 500 μl of the TBS was added to the upper end (donor chamber) of the glass cell, and 5 ml and of the TBS was added to the lower end (receiver chamber) of the glass cell. 200 μg of each of PDGFb or T-PDGFb was added to the upper end of the cell, and the porcine skin tissue was collected and disrupted. The content of PDGFb or T-PDGFb in the disrupted skin tissue was quantitatively analyzed using a human PDGF-BB ELISA Kit (DBB00, R&D system). Then, the content of T-PDGFb relative to the content of PDGFb was calculated as retention rate (see Table 12).

TABLE 12

Skin retention of fusion protein

| Treated protein | Retention (%) |
|---|---|
| PDGFb | 100 ± 25 |
| T-PDGFb | 11,300 ± 700 |

As can be seen in Table 12 above, the skin retention of T-PDGFb was about 110 times higher than that of PDGFb.

Thus, it can be seen that the use of the fusion protein of the present invention significantly increases the skin retention rate of PDGFb.

EXAMPLE 3-4

Verification of Effects of T-bFGF Fusion Protein

EXAMPLE 3-4-1

Verification of Effect on Collagen Expression

The effects of T-bFGF (synthesized in Example 2-4) and bFGF on the production of collagen and elastin were verified.

Specifically, fibroblasts were inoculated into a 6-well plate containing DMEM medium and were cultured for 24 hours to obtain a culture product showing a saturation degree of 70-80%. Various concentrations (1, 10 and 100 ng/ml) of T-bFGF or bFGF were added to the culture product and further cultured for 16 hours. After completion of the culture, the cultured cells were washed with PBS, and total RNA was isolated from the cells using an RNAeasy kit. The isolated total RNA was subjected to RT-PCR to obtain cDNA, and the obtained cDNA was subjected to real-time PCR, thereby quantitatively determining the expression level of collagen. As a control group, fibroblasts cultured without treatment with T-bFGF or bFGF were used, and as an internal control, GAP3DH mRNA was used (see Table 13).

TABLE 13

Effect of fusion protein on collagen expression

| Treated protein | Concentration of protein | Expression level (%) |
|---|---|---|
| Control | — | 100 ± 21 |
| bFGF | 10 ng/ml | 224 ± 15 |
|  | 100 ng/ml | 420 ± 25 |
| T-bFGF | 10 ng/ml | 250 ± 32 |
|  | 100 ng/ml | 490 ± 26 |

As can be seen in Table 13, when the cells were treated with bFGF or T-bFGF, the expression level of collagen in the cells increased compared to that in the control group. Also, the expression level of collagen in the treated cells treated with T-bFGF was higher than that in the cells treated with bFGF.

Thus, it can be seen that the use of the fusion protein of the present invention can increase the expression level of elastin compared to the use of bFGF alone.

EXAMPLE 3-4-2

Verification of Effect on Elastin Expression

The effect of T-bFGF or bFGF on the expression of elastin was verified in the same manner as described in Example 3-4-2, except that the expression level of elastin in place of collagen was quantitatively analyzed (see Table 14).

TABLE 14

Effect of fusion protein on elastin expression

| Treated protein | Concentration of protein | Expression level (%) |
|---|---|---|
| Control | — | 100 ± 14 |
| bFGF | 1 ng/ml | 95 ± 14 |
|  | 10 ng/ml | 220 ± 24 |
| T-bFGF | 1 ng/ml | 112 ± 10 |
|  | 10 ng/ml | 290 ± 24 |

As can be seen in Table 14, when the cells were treated with bFGF or T-bFGF, the expression level of elastin in the cells generally increased compared to that in the control group. Also, the expression level of elastin in the treated cells treated with T-bFGF was higher than that in the cells treated with bFGF.

Thus, it can be seen that the use of the fusion protein of the present invention can increase the expression level of elastin compared to the use of bFGF alone.

EXAMPLE 3-4-3

Verification of Skin Penetration

The skin penetration of the fusion protein was verified using Franz glass cell (standard diameter: 9 mm, receiver: 5 ml, Permegear).

Specifically, the porcine skin (0.7 mm thickness, Medikinetics) was placed between the upper and lower ends of the glass cell, and TBS (50 mM Tris pH 7.5, 150 mM NaCl) containing 1% BSA and 0.01% Tween 20 was prepared. Then, 500 µl of the TBS was added to the upper end (donor chamber) of the glass cell, and 5 ml and of the TBS was added to the lower end (receiver chamber) of the glass cell. Then, 200 µg of bFGF or T-bFGF was added to the upper end of the cell and allowed to react for 16 hours, after which the concentration of bFGF or T-bFGF at the lower end was quantitatively analyzed using a human FGFb ELISA kit (DGH00, R&D system), and the content of T-bFGF relative to the content of bFGF was calculated as penetration rate (see Table 15).

TABLE 15

Skin penetration rate (%) of fusion protein

| Treated protein | Retention (%) |
|---|---|
| bFGF | 100 ± 15 |
| T-bFGF | 513 ± 19 |

As can be seen in Table 15 above, the skin penetration rate of T-bFGF was about 5 times higher than that of bFGF.

Thus, it can be seen that the use of the fusion protein of the present invention significantly increases the skin penetration of bFGF.

EXAMPLE 3-4-4

Verification of Skin Retention

The skin retention of the fusion protein was verified using Franz glass cell (standard diameter: 9 mm, receiver: 5 ml, Permegear).

Specifically, the porcine skin (0.7 mm thickness, Medikinetics) was placed between the upper and lower ends of the glass cell, and TBS (50 mM Tris pH 7.5, 150 mM NaCl) containing 1% BSA and 0.01% Tween 20 was prepared. Then, 500 µl of the TBS was added to the upper end (donor chamber) of the glass cell, and 5 ml and of the TBS was added to the lower end (receiver chamber) of the glass cell. 200 µg of each of bFGF or T-bFGF was added to the upper end of the cell, and the porcine skin tissue was collected and disrupted. The content of bFGF or T-bFGF in the disrupted skin tissue was quantitatively analyzed using a human bFGF ELISA Kit (DBB50, R&D system). Then, the content of T-PDGFb relative to the content of bFGF was calculated as retention rate (see Table 16)

TABLE 16

Skin retention of fusion protein

| Treated protein | Retention (%) |
|---|---|
| bFGF | 100 ± 25 |
| T-bFGF | 9,800 ± 210 |

As can be seen in Table 16 above, the skin retention of T-bFGF was about 100 times higher than that of hGH.

Thus, it can be seen that the use of the fusion protein of the present invention significantly increases the skin retention rate of bFGF.

As described above, the fusion protein of the present invention, which comprises the skin-penetrating peptide fused to a physiologically active protein, significantly enhances the skin penetration and skin retention of the physiologically active protein while maintaining or enhancing the ability of the physiologically active protein to synthesize substances, for example, collagen, elastin, laminin and HAS2, which show useful effects such as skin wrinkle reduction. Thus, the fusion protein of the present invention can be widely used as an active ingredient in functional cosmetic compositions and pharmaceutical compositions for external skin use.

What is claimed is:

1. A fusion protein comprising a skin-penetrating peptide comprising the amino acid sequence of SEQ ID NO: 1 and a physiologically active protein selected from the group consisting of human growth hormone (hGH), epidermal growth factor (EGF), platelet-derived growth factor-b subunit (PDGFb) and basic fibroblast growth factor (bFGF).

2. The fusion protein of claim 1, wherein the skin-penetrating peptide is bound to the N-terminus of the physiologically active protein.

3. The fusion protein of claim 2, wherein the skin-penetrating peptide is bound to the N-terminus of the physiologically active protein by a linker.

4. The fusion protein of claim 1, wherein the physiologically active protein comprises the amino acid sequence selected from the group consisting of SEQ ID NO: 2, 3, 4 and 5.

5. The fusion protein of claim 1, wherein the fusion protein comprises an amino acid sequence selected from the group consisting of the amino acid sequences of SEQ ID NO: 6 to SEQ ID NO: 9.

6. A composition for improving skin conditions, comprising a fusion protein as an active ingredient,
wherein the fusion protein comprises a physiologically active protein and a skin-penetrating peptide having the amino acid sequence of SEQ ID NO: 1, wherein the physiologically active protein is selected from the group consisting of human growth hormone (hGH), epidermal growth factor (EGF), platelet-derived growth factor-b subunit (PDGFb) and basic fibroblast growth factor (bFGF).

* * * * *